United States Patent
List

(10) Patent No.: US 11,241,533 B2
(45) Date of Patent: Feb. 8, 2022

(54) DEVICE FOR MEASURING A FILL LEVEL OF A FLEXIBLE MEDICINE RESERVOIR

(71) Applicant: Roche Diabetes Care, Inc., Indianapolis, IN (US)

(72) Inventor: Hans List, Oberzent (DE)

(73) Assignee: ROCHE DIABETES CARE, INC., Indianapolis, IN (US)

(*) Notice: Subject to any disclaimer, the term of this patent is extended or adjusted under 35 U.S.C. 154(b) by 11 days.

(21) Appl. No.: 16/326,738

(22) PCT Filed: Jun. 22, 2017

(86) PCT No.: PCT/EP2017/065441
§ 371 (c)(1),
(2) Date: Feb. 20, 2019

(87) PCT Pub. No.: WO2018/041437
PCT Pub. Date: Mar. 8, 2018

(65) Prior Publication Data
US 2019/0184098 A1   Jun. 20, 2019

(30) Foreign Application Priority Data
Sep. 5, 2016  (EP) .................................. 16187275

(51) Int. Cl.
*A61M 5/168* (2006.01)
*A61M 5/148* (2006.01)
(Continued)

(52) U.S. Cl.
CPC .......... *A61M 5/1684* (2013.01); *A61M 5/148* (2013.01); *G01F 23/16* (2013.01);
(Continued)

(58) Field of Classification Search
CPC ................ A61M 5/1684; A61M 5/184; A61M 2205/0216; A61M 2205/3306;
(Continued)

(56) References Cited

U.S. PATENT DOCUMENTS 4,596,558 A * 6/1986 Smith ............... A61M 5/16809
604/134
5,810,783 A 9/1998 Claro
(Continued)

FOREIGN PATENT DOCUMENTS

| RU | 2315961 | 1/2008 |
| RU | 2010107861 | 9/2011 |
| RU | 2013142999 | 3/2015 |

OTHER PUBLICATIONS

Office Action for related JP2019-511694 dated Mar. 30, 2021.

*Primary Examiner* — James D Ponton
(74) *Attorney, Agent, or Firm* — Woodard, Emhardt, Henry, Reeves & Wagner, LLP

(57) ABSTRACT

The invention concerns a device (1) for measuring a fill level of a flexible medicine reservoir (6). The device (1) comprises a support (2) for supporting the flexible medicine reservoir (6) and a leaf spring member (3). A first section (31) of the leaf spring member (3) is mounted to a fixed bearing. A second section (32) of the leaf spring member (3) is guided by a floating bearing. The leaf spring member (3) is designed for contacting the flexible medicine reservoir (6) and for providing that changes in the fill level of the flexible medicine reservoir (6) effect changes of the form of the leaf spring member (3). A detector (5) is arranged for detecting the effected changes of the form of the leaf spring member (3) and for enabling measuring of the fill level of the flexible medicine reservoir (6).

21 Claims, 2 Drawing Sheets

(51) Int. Cl.
*G01F 23/16* (2006.01)
*G01F 23/00* (2006.01)

(52) U.S. Cl.
CPC ............... *A61M 2205/0216* (2013.01); *A61M 2205/3306* (2013.01); *A61M 2205/3317* (2013.01); *A61M 2205/3327* (2013.01); *A61M 2205/3389* (2013.01); *A61M 2207/00* (2013.01); *G01F 23/003* (2013.01)

(58) Field of Classification Search
CPC .. A61M 2205/3317; A61M 2205/3327; A61M 2205/3389; A61M 5/148; A61M 5/1483; A61M 5/1486; A61M 5/152; A61M 5/155; G01F 23/26; G01F 23/003
USPC ........................ 73/290 R, 305, 306, 307, 308
See application file for complete search history.

(56) References Cited

U.S. PATENT DOCUMENTS

| | | | |
|---|---|---|---|
| 6,578,417 | B1 | 6/2003 | Eck |
| 6,990,860 | B1* | 1/2006 | Gillanders ................ A45F 3/20 222/175 |
| 7,322,233 | B2 | 1/2008 | Fehrenbach et al. |
| 8,179,125 | B2 | 5/2012 | Benner et al. |
| 8,286,484 | B2 | 10/2012 | Stroder |
| 8,466,693 | B2 | 6/2013 | Osswald et al. |
| 9,222,828 | B2 | 12/2015 | Lienenkamp |
| 2008/0097343 | A1* | 4/2008 | Woehr ................ A61M 5/3273 604/263 |
| 2008/0215029 | A1 | 9/2008 | Rake et al. |
| 2010/0174236 | A1* | 7/2010 | Burns ................ A61M 5/3213 604/110 |
| 2011/0107853 | A1 | 5/2011 | Studer |

* cited by examiner

DEVICE FOR MEASURING A FILL LEVEL OF A FLEXIBLE MEDICINE RESERVOIR

FIELD OF THE INVENTION

The present invention relates to a device for measuring a fill level of a flexible medicine reservoir. The invention also relates to a medical infusion device comprising a device according to the invention.

BACKGROUND ART

Medical infusion devices, such as insulin pumps, often comprise a rigid container for storing the medicine. The container serves as a reservoir for the medicine as well as a dosing device. Containers can have the form of a cylinder having arranged a plunger. In order to alert a user when a fill level of a container falls below a minimum, the remaining amount of medicine stored in the container of an infusion device needs to be monitored. For example, the position of the plunger in the container can be visually monitored, or an electric signal relating to the position of the plunger can be recorded and used to control a display for displaying the remaining amount of medicine. Displaying the remaining amount of medicine is simple for infusion devices having installed a rigid container with a plunger as described above. However, because of the strongly varying friction between the plunger and the cylinder of such containers, it is difficult to discharge small amounts of medicine.

In order to provide a more sensitive infusion device enabling the discharge of small amounts of medicine, a flexible medicine reservoir can be arranged. The flexible medicine reservoir can have the form of a bag. A pump can be used as a dosing device. The pump fills its chamber from the flexible medicine reservoir and discharges the medicine filled in the chamber in order to administer the medicine to the patient. Because of a small pressure difference between the flexible medicine reservoir and the environment, small amounts of medicine can be administered precisely. However, the remaining amount of medicine in the flexible medicine reservoir cannot be determined easily. The flexible medicine reservoir can be visibly arranged in the infusion device, but a user cannot easily determine the remaining amount of medicine from the geometry of the flexible medicine reservoir. For example, in case the flexible medicine reservoir has the form of a bag, it is very difficult to estimate the remaining amount of medicine from the shape of the bag. Moreover, contrary to a container in the form of a cylinder with a plunger, the flexible medicine reservoir in the form of a bag, for example, includes no mechanical element that could be used to record an electric signal in order to determine the remaining amount of medicine in the flexible medicine reservoir.

US20110107853 discloses determining a fill level of an inflow-less flexible medicine reservoir. The inflow-less flexible medicine reservoir has a monotonically decreasing fill level. A stop surface can be designed and arranged such that the stop surface contacts the inflow-less flexible medicine reservoir while the inflow-less flexible reservoir is filled above a predetermined level. A release detector can generate an output signal indicative of contact between the stop surface and the inflow-less flexible medicine reservoir being released and a processing unit can determine the fill level of the inflow-less flexible medicine reservoir from an output signal of the release detector. Because of the stop surface, the inflow-less flexible medicine reservoir cannot be inflated to the same volume as without the stop surface. Accordingly, only a smaller amount of medicine can be stored in the inflow-less flexible medicine reservoir and the reservoir needs to be enlarged in order to store the same amount of medicine as can be stored in a reservoir that has not arranged a stop-surface.

According to another solution for determining the fill level of a flexible medicine reservoir, a first electrode is arranged on the flexible medicine reservoir. The fill level is determined by capacitively detecting the distance between the first electrode and a counter electrode. The counter electrode can be arranged on a wall surrounding the flexible medicine reservoir. In another variant, the counter electrode can be arranged on the flexible medicine reservoir opposite the first electrode. Measuring the capacitance of the electrodes is sensitive to environmental noise such as noise induced by body parts of a human, metal objects, etc. and the detection of the distance between the electrodes is therefore difficult. As an electrode has to be arranged on the flexible medicine reservoir, manufacturing costs are increased. Mechanical properties of the flexible medicine reservoir are changed by the electrode, wherein a larger reservoir may be required to store the same amount of medicine as can be stored in a reservoir that has not arranged an electrode.

DISCLOSURE OF THE INVENTION

It is an object of the present invention to provide a device for measuring a fill level of a flexible medicine reservoir, which device does not have at least some of the disadvantages of the prior art. In particular, it is an object of the present invention to provide a device for measuring a fill level of a flexible medicine reservoir, which device enables precise monitoring of the fill level of the flexible medicine reservoir. In particular, it is an object of the present invention to provide a device for measuring a fill level of a flexible medicine reservoir, which device enables precise monitoring of the fill level of a standard flexible medicine reservoir that is designed to deliver medicine to a medical pump and/or receive medicine from a medical pump. In particular, it is an object of the present invention to provide a device for measuring the fill level of a flexible medicine reservoir, which device enables precise monitoring of the fill level of the flexible medicine reservoir and has a simple design.

According to the present invention, these objects are achieved through the features of the independent claims. In addition, further advantageous embodiments follow from the dependent claims and the description.

According to the present invention, the above-mentioned objects are particularly achieved by a device for measuring a fill level of a flexible medicine reservoir that comprises a support for supporting the flexible medicine reservoir and a leaf spring member. A first section of the leaf spring member is mounted to a fixed bearing. A second section of the leaf spring member is guided by a floating bearing. The leaf spring member is designed for contacting the flexible medicine reservoir and for providing that changes of the fill level of the flexible medicine reservoir effect changes of the form of the leaf spring member. A detector is arranged for detecting the effected changes of the form of the leaf spring member and for enabling measuring of the fill level of the flexible medicine reservoir. The fixed bearing can enable a rotational motion of the first section. The floating bearing can enable a guided motion of the second section. Accordingly, changes of the form of the leaf spring is enabled in accordance to the changes of the fill level of the flexible medicine reservoir. In particular, the fill level of the flexible medicine reservoir effects volume changes of the flexible medicine reservoir, which in turn effects changes of the form of the leaf spring member contacting the flexible medicine reservoir. In particular a rotational motion of the first section can be precisely detected for enabling measuring of the fill level of the flexible medicine reservoir.

In an embodiment, the device is further designed such that when the fill level of the flexible medicine reservoir changes between essentially empty and essentially full, the form of the leaf spring member changes between an arc-shaped form and a substantially flat-shaped form.

In an embodiment, the fixed bearing has the design of a hinge bearing, in particular the first part is connected to one or more barrel sections that are rotationally mounted on a pivot that is fixedly arranged with respect to the support. The hinge bearing enables a rotational motion of the first section.

In an embodiment, the floating bearing has the design of a slide bearing, in particular the second part is connected to a guided section that can slide along a fixed portion that is fixedly arranged relative to the support. The slide bearing enables a guided motion of the second section, in particular a guided motion along a curve such as a line.

The leaf spring member has a flexible design. The flexible medicine reservoir contacts the leaf spring member. When the flexible medicine reservoir is filled with medicine, the volume increases. The leaf spring member is arranged such that because of the increased volume the flexible medicine reservoir pushes against the leaf spring member and deforms the leaf spring member. The flexible medicine reservoir pushes against the spring forces of the leaf spring member. When medicine is withdrawn from the flexible medicine reservoir, the volume decreases. Due to the spring forces, the form of the leaf spring member changes. The leaf spring member keeps contact with the flexible medicine reservoir. The leaf spring member can change its form because the first section can perform a rotational motion and because the second section can perform a guided motion, in particular a guided motion along a curve such as a line.

In an embodiment, the flexible medicine reservoir is arranged between the support and the leaf spring member. The leaf spring member is arranged such that the spring forces effect the contact with the flexible medicine reservoir. Accordingly, the leaf spring member can follow the volume changes of the flexible medicine reservoir due to filling medicine into the reservoir and depleting medicine from the reservoir.

In a variant, the leaf spring member is fabricated from a sheet material. In particular, the costs for the leaf spring member are low.

In a variant, the leaf spring member includes at least one of: cut-outs, and breakthroughs. In particular, mechanical properties of the leaf spring member can be optimized, such as flexibility, spring forces, danger of damaging the flexible medicine reservoir, etc.

In a variant, the leaf spring member includes a contact section for contacting the flexible medicine reservoir, wherein the contact section is located between the first section and the second section. In particular, the contact section can be optimized for contacting the flexible medicine reservoir, the first section can be optimized for enabling a rotational motion, and the second section can be optimized for enabling a guided motion. Optimization can be achieved by forming the leaf spring member accordingly, such as by arranging appropriate cut-outs, breakthroughs, etc.

In a variant, the detector is designed for detecting a rotational motion of the first section about the fixed bearing. Rotational motion can be detected precisely. Precise measuring of the fill level is further improved.

In an embodiment, the detector includes at least one of a magnetic, an optic, and a mechanical detector for detecting the changes in the form of the leaf spring member.

In an embodiment, the detector includes a magnetic sensor fixedly arranged with respect to the support, wherein the magnetic sensor is designed to cooperate with a magnetic element which is fixed to the leaf spring member in such a manner that the magnetic element follows a rotational motion of the first part effected because of the changes of the form of the leaf spring member.

In a variant, the device further comprises a processing unit for receiving an electric signal from the detector and for transforming the electric signal into a fill level of the flexible medicine reservoir.

The invention also relates to a medical infusion device comprising a device in accordance to the invention, wherein the flexible medicine reservoir is designed to deliver medicine to the medical pump and/or to receive medicine from the medical pump. Medicine can be withdrawn from the reservoir and refilled, wherein the fill level of the flexible medicine reservoir can be precisely measured.

In an embodiment, the medical pump is an insulin pump, and wherein the flexible medicine reservoir is designed to store a medicine that includes insulin.

The invention further relates to a method for measuring a fill level of a flexible medicine reservoir being supported by a support. The method comprises: providing that changes in the fill level of the flexible medicine reservoir effect changes of the form of a leaf spring member, and detecting the effected changes of the form of the leaf spring member for measuring the fill level of the flexible medicine reservoir. In order to provide that changes in the fill level of the flexible medicine reservoir effect changes of the form of the leaf spring member, a first section of the leaf spring member can be mounted to a fixed bearing, a second section of the leaf spring member can be guided by a floating bearing, and the leaf spring member can be designed for contacting the flexible medicine reservoir. For detecting the changes of the form of the leaf spring member, a detector can be arranged for detecting the effected changes of the form of the leaf spring member and for enabling measuring the fill level of the flexible medicine reservoir. In particular, the changes of the form of the leaf spring member are caused by changes of the thickness of the reservoir, which depends on the fill level. In particular, detecting the effected changes of the form of the leaf spring member relate to the detection of a rotational movement of a section of the leaf spring member, wherein the rotational movement is detected by the detection of a change of an angle.

BRIEF DESCRIPTION OF THE DRAWINGS

The herein described invention will be more fully understood from the detailed description given herein below and the accompanying drawings which should not be considered limiting to the invention described in the appended claims. The drawings are showing:

MODE(S) FOR CARRYING OUT THE INVENTION

Figure 1:
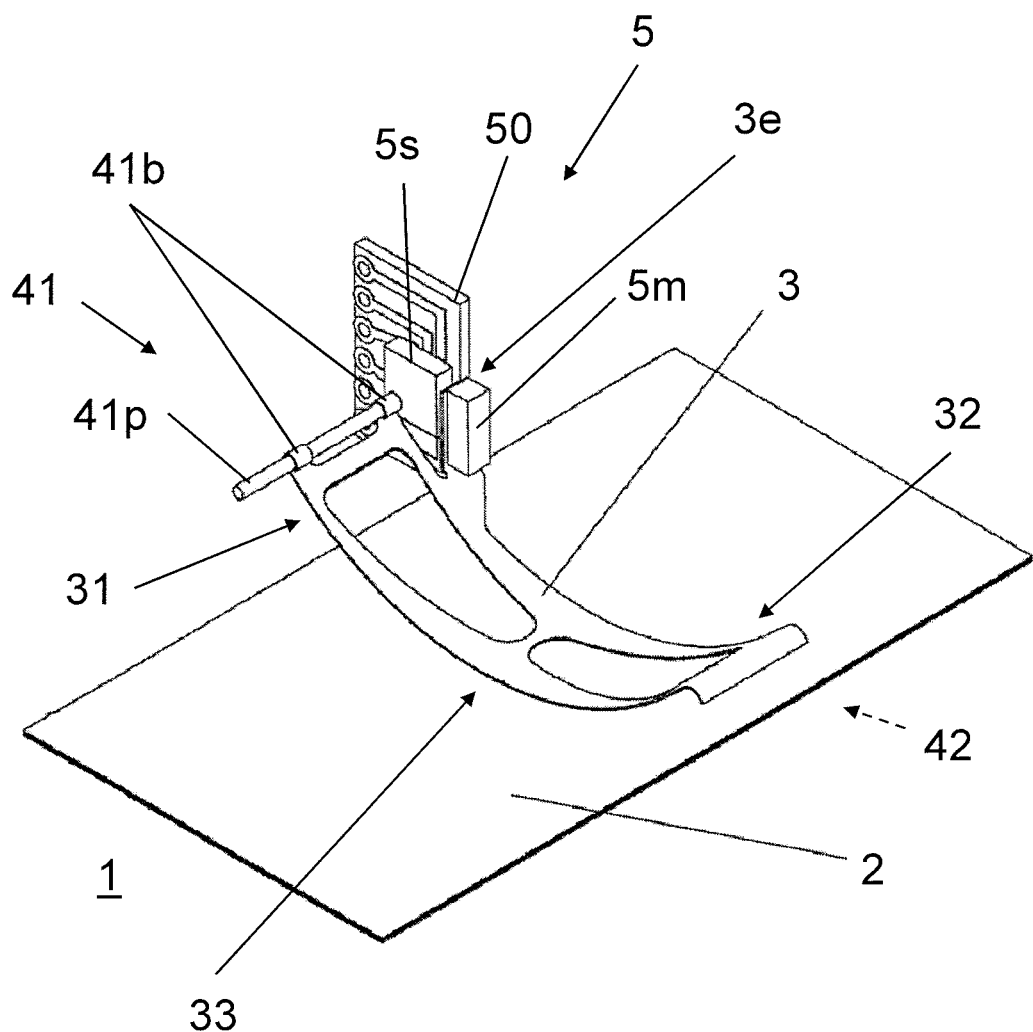
FIG. 1 illustrates schematically a perspective view of a device for measuring a fill level of a flexible medicine reservoir.

FIG. 1 illustrates schematically a perspective view of a device 1 for measuring a fill level of a flexible medicine reservoir. The device 1 comprises a support 2 for supporting the flexible medicine reservoir. The flexible medicine reservoir is not illustrated in FIG. 1. The device 1 comprises a leaf spring member 3. In the embodiment illustrated in FIG. 1, the leaf spring member 3 is in an unstressed state. The leaf spring member 3 has an arc-shaped form in the unstressed state. As illustrated in FIG. 1, the arc-shaped form of the leaf spring member 3 can extend down to the support 2.

A first section 31 of the leaf spring member 3 is mounted to a fixed bearing. As illustrated in FIG. 1, the fixed bearing has the form of a hinge bearing 41. As will be described in more detail below, a second section 32 of the leaf spring member 3 is guided by a floating bearing. The floating bearing can have the form of a slide bearing 42. Neither the floating bearing nor the slide bearing 42 are illustrated in FIG. 1, which is indicated by a dashed arrow instead of a normal arrow.

The first section 31 of the leaf spring member 3 can form one end of the leaf spring member 3. The second section 32 of the leaf spring member 3 can form another end of the leaf spring member 3.

The first section 31 of the leaf spring member 3 can rotate about an axis defined by the fixed bearing, which can have the form of the hinge bearing 41. As illustrated in FIG. 1, the hinge bearing 41 includes a pivot 41p and barrel sections 41b. As will be described in more detail below, the pivot 41p is fixedly mounted relative to the support 2. The barrel sections 41b are fixedly connected to the leaf spring member 3. The pivot 41p extends through the barrel sections 41b and defines the axis about which the first section 31 of the leaf spring member 3 can rotate. One or more barrel sections 41b can be arranged.

The fixed bearing can have the form of a hinge bearing 41. The floating bearing can have the form of a slide bearing 42. The hinge bearing 41 enables rotational motions of the first section 31 of the leaf spring member 3. The slide bearing 42 enables guided motions of the second section 32 of the leaf spring member 3 in a direction defined by the slide bearing 42. The flexible medicine reservoir, which is not shown in FIG. 1, can be arranged between the support 2 and the leaf spring member 3. When the volume of the flexible medicine reservoir is small, for example when the flexible medicine reservoir is essentially empty, the leaf spring member 3 has an arc-shaped form, as illustrated in FIG. 1. The flexible medicine reservoir is supported by the support 2, which is fixedly arranged. The flexible medicine reservoir contacts the leaf spring member 3, which has a flexible design. When medicine is filled into the flexible medicine reservoir, the volume of the flexible medicine reservoir increases. The flexible medicine reservoir pushes the leaf spring member 3 upwards and effects changes of the form of the leaf spring member 3. In particular, the first section 31 of the leaf spring member rotates about the hinge bearing 41 and the second section 32 of the leaf spring member 3 slides along the slide bearing 42.

As schematically illustrated in FIG. 1, the device 1 for measuring a fill level of a flexible medicine reservoir includes a detector 5 for detecting the effected changes of the form of the leaf spring member 3 and for enabling measuring the fill level of the flexible medicine reservoir 6. The detector 5 includes a mounting 5o which is fixedly arranged relative to the support 2. The mounting 5o can include a sensor, such as a magnetic sensor, an optic sensor, a mechanical sensor, etc., for sensing changes of the form of the leaf spring member 3, in particular a rotational motion of the first section 31 of the leaf spring member 3. The sensor is designed to generate an electric signal in accordance to the changes of the form of the leaf spring member 3, in particular a rotational motion of the first section 31 of the leaf spring member 3. As illustrated in FIG. 1, the mounting 5o can include electric lines or wires for transmitting electric signals and/or electric energy.

In the embodiment illustrated in FIG. 1, a magnetic sensor 5s is fixed to the mounting 5o. The magnetic sensor 5s cooperates with a magnetic element 5m. The magnetic element 5m is fixed to the leaf spring member 3, in particular to the first section 31 of the leaf spring member 3. For example, as illustrated in FIG. 1, the design of the leaf spring member 3 can include a small plate 3e bent off from the first section 31, wherein the magnetic element 5m can be fixed to the plate, for example by gluing, bonding, etc. The magnetic element 5m performs a rotational motion about the magnetic sensor 5s in accordance to the rotational motion of the first section 31 of the leaf spring member 3. The magnetic sensor 5s can generate a signal related to the rotational motion of the magnetic element 5m. The changes of the fill level of the flexible medicine reservoir effect changes in the form of the leaf spring member 3 and a rotational motion of the first section 31 of the leaf spring member 3, in particular a rotational motion about the axis defined by pivot 41p. Accordingly, the signal generated by the magnetic sensor 5s, which cooperates with the magnetic element 5m, is related to the fill level of the flexible medicine reservoir.

Figure 2A:
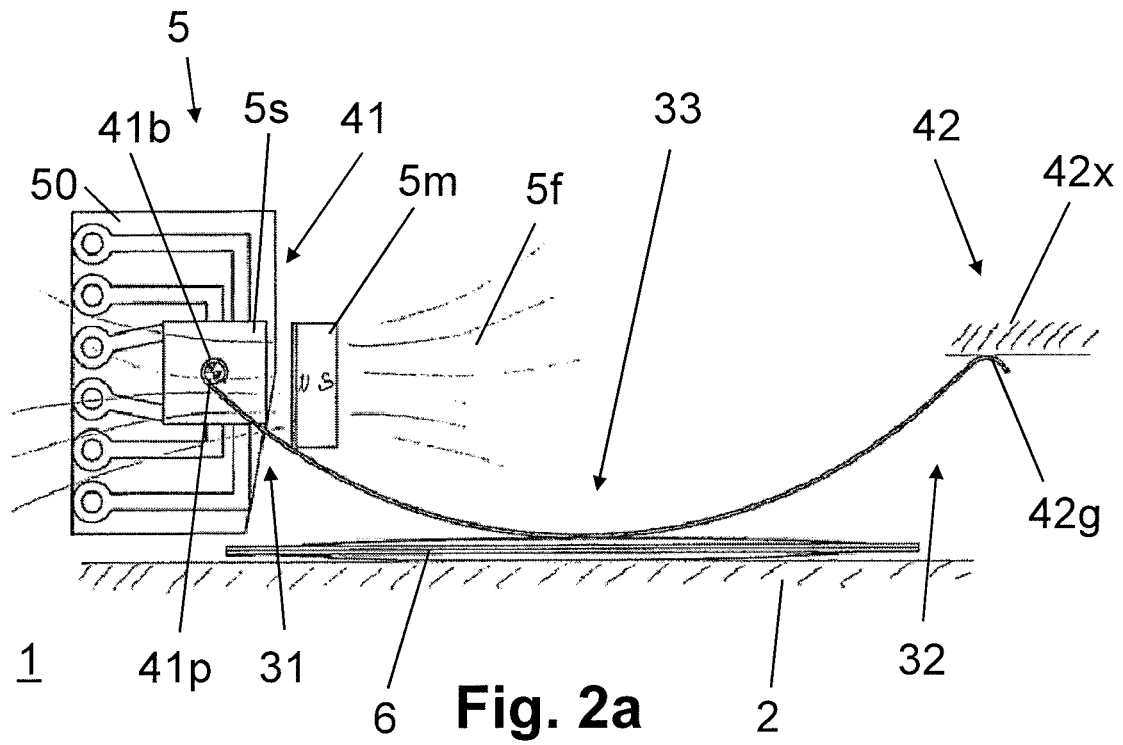
FIG. 2a illustrates schematically a device for measuring the fill level of a flexible medicine reservoir which is essentially empty.

FIG. 2a illustrates schematically a device 1 for measuring the fill level of a flexible medicine reservoir 6. The flexible medicine reservoir 6 illustrated in FIG. 2a is essentially empty.

Figure 2B:
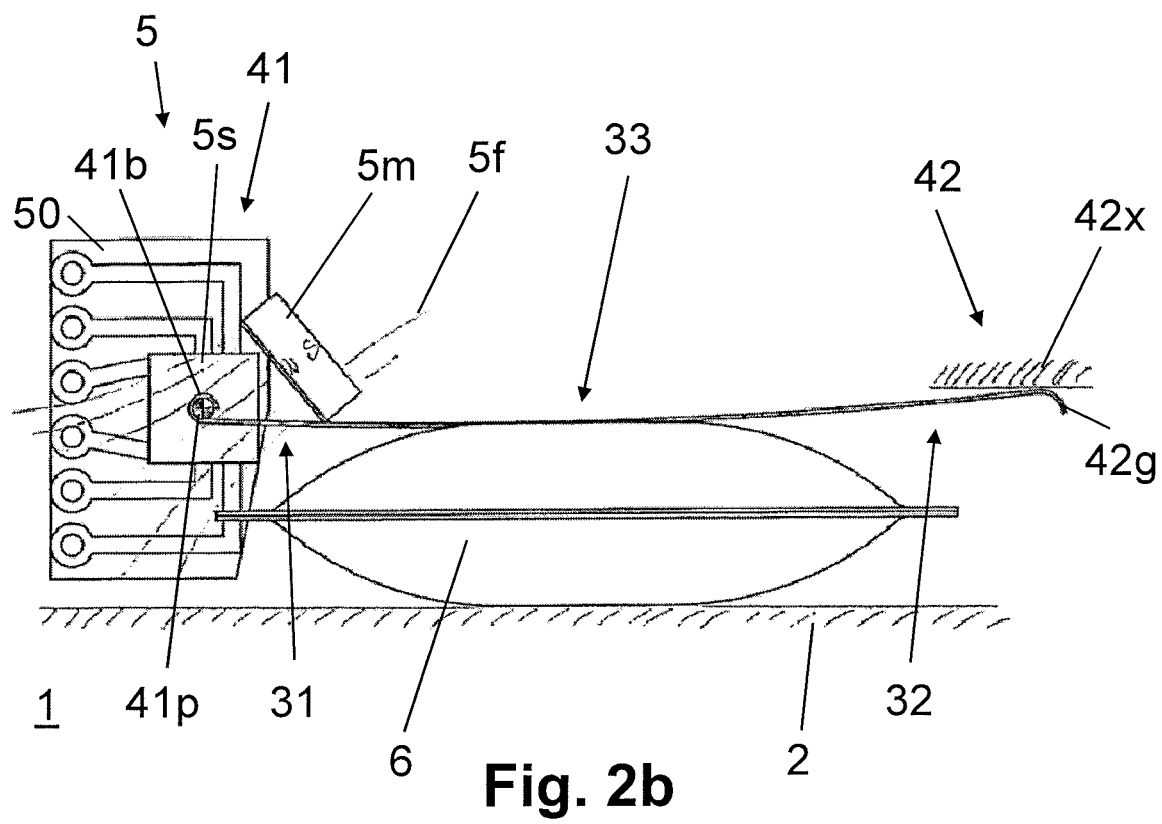
FIG. 2b illustrates schematically a device for measuring the fill level of a flexible medicine reservoir which is essentially fully filled with the medicine.

FIG. 2b illustrates schematically a device 1 for measuring the fill level of a flexible medicine reservoir 6. The flexible medicine reservoir 6 illustrated in FIG. 2b is essentially fully filled with the medicine.

As illustrated in FIG. 2a, the leaf spring member 3, in particular the contact section 33 of the leaf spring member 3, contacts the essentially empty flexible medicine reservoir 6. The leaf spring member 3 illustrated in FIG. 2a is in an essentially unstressed state. The leaf spring member 3 has an arc-shaped form in the unstressed state.

As illustrated in FIG. 2b, the leaf spring member 3, in particular the contact section 33 of the leaf spring member 3, contacts the flexible medicine reservoir 6, which is essentially fully filled with the medicine. The leaf spring member 3 illustrated in FIG. 2b is in an essentially fully stressed state. The leaf spring member 3 has a substantially flat-shaped form in the essentially fully stressed state.

The form of the leaf spring member 3 illustrated in FIG. 2a and FIG. 2b is significantly different.

The material of the leaf spring member 3 and the dimensions such as the thickness of the leaf spring member 3 provide that the leaf spring member 3 has a flexible spring design. The flexi-ble spring design is such that external forces to the leaf spring member 3 can effect that the leaf spring member 3 can be brought from the essentially unstressed state into the essentially fully stressed state, or any state there between. The flexible spring design is such that absence of external forces, spring forces of the leaf spring member 3 effect that the leaf spring member 3 returns automatically from the fully stressed state, or any state below the fully stressed state, into the essentially unstressed state. Between the essentially unstressed state and the essentially fully stressed state, the leaf spring member 3 changes its form between an arc-shaped form and a substantially flat-shaped form, wherein the arc-shaped form corresponds to the essentially unstressed state and the substantially flat-shaped form corresponds to the essentially fully stressed state.

When the flexible medicine reservoir 6 is essentially fully filled with the medicine, the spring forces of the leaf spring member 3 put a pressure on the flexible medicine reservoir 6. The flexible spring design of the leaf spring member 3 can be adapted to the flexible medicine reservoir 6 in such manner that the leaf spring member 3 essentially palpates the flexible medicine reservoir 6, but does not noteworthy deform the leaf spring member 3 or apply a significant stress to the leaf spring member 3. Usually, spring forces of some ten milli-Newton, such as between ten and fifty milli-Newton, preferably between ten and thirty milli-Newton, are sufficient.

The leaf spring member 3 needs to provide only small spring forces. Accordingly, the leaf spring member 3 can have a thin design enabling that the available space for the flexible medicine reservoir is essentially not reduced. For example, the fully filled flexible medicine reservoir can extend essentially from one wall of the housing of a medical infusion device to another wall, wherein, because of the thin design, the leaf spring member 3 does not reduce the available space.

As illustrated in FIG. 2a and FIG. 2b, the first section 31 of the leaf spring member 3 is mounted to the fixed bearing in the form of a hinge bearing 41. The second section 32 of the leaf spring member 3 is guided by the floating bearing in the form of a slide bearing 42. The hinge bearing 41 includes the pivot 41p, which is fixedly mounted relative to the support 2. The pivot 41p has mounted the barrel sections 41b, which are connected to the first section 31 of the leaf spring member 3. The slide bearing 42 includes the guided section 42g that can slide along the fixed portion 42x. The fixed portion 42x is fixedly mounted relative to the support 2. The guided section 42g is connected to the second section 32 of the leaf spring member 3. The guided section 42g that can slide along the fixed portion 42x in an essentially horizontal direction relative to the support 2. For providing a smooth and long-term operation of the slide bearing 42, as illustrated in FIG. 2a and FIG. 2b, the guided section 42g can have a curved shape and the fixed portion 42x can have a flat surface.

The flexible medicine reservoir 6 illustrated in FIG. 2a is essentially empty. The leaf spring member 3 has an arc-shaped form. By filling medicine into the flexible medicine reservoir 6, the volume of the flexible medicine reservoir 6 increases. The contact section 33 of the leaf spring member 3 is pushed upwards away from the support 2 and effects a deformation of the leaf spring member 3. The first section 31 rotates about the axis defined by the pivot 41p of the hinge bearing 41. The second section 32 slides in horizontal direction along the fixed portion 42x of the slide bearing 42. Spring forces of the leaf spring member 3 increase. The flexible medicine reservoir 6 illustrated in FIG. 2b is essentially fully filled with medicine. The leaf spring member 3 has a substantially flat-shaped form.

As illustrated in FIG. 2a and FIG. 2b, the mounting 5o is arranged in a fixed position relative to the support 2. The magnetic sensor 5s is fixed to the mounting 5o. The magnetic sensor 5s cooperates with the magnetic element 5m. The magnetic element 5m is fixed to the leaf spring member 3, in particular to the first section 31 of the leaf spring member 3. As illustrated in FIG. 2a and in FIG. 2b, when the flexible medicine reservoir 6 is essentially empty according to FIG. 2a, the magnetic element 5m has a different relative position to the magnetic sensor 5s than when the flexible medicine reservoir 6 is essentially fully filled with the medicine according to FIG. 2b. As illustrated in FIG. 2a and FIG. 2b, the magnetic field lines 5f of the magnetic element 5m cross the magnetic sensor 5s in an inclination that depends on the fill level of the flexible medicine reservoir 6. The change in inclination of the magnetic field lines 5f can be detected with the magnetic sensor 5s, which can have a small, cheap and robust design. Magnetic sensors 5s having such a design are available off-the-shelf.

The magnetic sensor 5s can have a design providing that two coupled signals are generated which depend on the direction of the magnetic field, for example two voltages that are proportional to the sine and cosine of the angle of the magnetic field relative to the magnetic sensor 5s. By determining the ratio between these two signals, eliminated can be the dependency on the absolute field strength of the magnetic field at the magnetic sensor.

Alternatively or additionally, two hall effect sensors can be arranged for detecting the magnetic field of the magnetic element 5m. The two hall effect sensors can be arranged perpendicular to each other.

The small plate 3e bent off from the leaf spring member 3, as illustrated in FIG. 1, can be designed to include a mirror instead or additionally to providing a fixture for the magnetic element 3m. The mirror can cooperate with a light source and a light detector, such as a LED (Light Emitting Diode) and a photo detector, in such a manner that the signal of the light detector relates to an angle of the first section 31 respectively to the fill level of the flexible medicine reservoir 6.

Alternatively or additionally, a mechanical design, for example based on a potentiometer, can enable measuring of the fill level of the flexible medicine reservoir 6.

The device 1 for measuring the fill level of the flexible medicine reservoir 6 can be calibrated. First, an empty flexible medicine reservoir is arranged and the measured fill level is recorded. Then, the flexible medicine reservoir is filled with medicine, wherein the volume of the filled in medicine and the measured fill level are recorded. In a variant, calibration can be performed by the user at least partly. For example, the user can fill medicine into the flexible medicine reservoir and can record the volume of the filled in medicine together with the change of the measured fill level. For example, tolerances in the design of the flexible medicine reservoir can be accounted for.

During operation of the device 1, medicine can be withdrawn from the flexible medicine reservoir and refilled. For example, a unused amount of medicine in a pump can be refilled into the flexible medicine reservoir, wherein the device 1 can correctly measure the fill level of the flexible medicine reservoir, contrary to the prior art such as US20110107853.

The first section 31, the contact section 33 and the second section 32 of the leaf spring member 3 can follow one after the other. In other words, the contact section 33 can be located between the first section 31 and the second section 32. However, as the skilled person understands, a more precise definition of the geometry of the first section 31, the contact section 33 and the second section 32 is not required.

The leaf spring member 3 can include cut-outs or breakthroughs, as illustrated in FIG. 1, in order to provide required mechanical properties of the leaf spring member 6 such as the flexibility, stability, surface of contact with the flexible medicine reservoir, etc.

The invention claimed is:

1. A device for measuring a fill level of a flexible medicine reservoir, comprising:
   a support for supporting the flexible medicine reservoir;
   a leaf spring member having a form,
      wherein a first section of the leaf spring member is mounted to a fixed bearing, wherein a second section of the leaf spring member is guided by a floating bearing, wherein the leaf spring member is designed for contacting the flexible medicine reservoir, changes in the fill level of the flexible medicine reservoir effecting changes of the form of the leaf spring member; and
   a detector arranged for detecting the effected changes of the form of the leaf spring member and for enabling measuring of the fill level of the flexible medicine reservoir,
   wherein the device further includes at least one selected from the group consisting of:
      a) the fixed bearing is a hinge bearing, the first section being connected to one or more barrel sections that are rotationally mounted on a pivot that is fixedly arranged with respect to the support,
      b) the floating bearing is a slide bearing, the second section being connected to a guided section that can slide along a fixed portion that is fixedly arranged relative to the support,
      c) the detector is designed for detecting a rotational motion of the first section about the fixed bearing, and
      d) the detector includes a magnetic sensor fixedly arranged with respect to the support, wherein the magnetic sensor is designed to cooperate with a magnetic element which is fixed to the leaf spring member in such a manner that the magnetic element follows a rotational motion of the first part effected because of the changes of the form of the leaf spring member.

2. The device according to claim 1, further designed such that the form of the leaf spring member is an arc-shaped form when the fill level of the flexible medicine reservoir is essentially empty and wherein the form of the leaf spring member is a substantially flat-shaped form when the fill level of the flexible medicine reservoir is essentially full.

3. The device according to claim 1, wherein the fixed bearing is a hinge bearing, the first section being connected to one or more barrel sections that are rotationally mounted on a pivot that is fixedly arranged with respect to the support.

4. The device according to claim 3, wherein the floating bearing is a slide bearing, the second section being connected to a guided section that can slide along a fixed portion that is fixedly arranged relative to the support.

5. The device according to claim 3, wherein the detector includes a magnetic sensor fixedly arranged with respect to the support, wherein the magnetic sensor is designed to cooperate with a magnetic element which is fixed to the leaf spring member in such a manner that the magnetic element follows a rotational motion of the first part effected because of the changes of the form of the leaf spring member.

6. The device according to claim 1, wherein the flexible medicine reservoir is arranged between the support and the leaf spring member.

7. The device according to claim 1 wherein the leaf spring member is fabricated from a sheet material.

8. The device according to claim 1, wherein the leaf spring member includes at least one of: cut-outs, and break-throughs.

9. The device according to claim 1, wherein the leaf spring member includes a contact section for contacting the flexible medicine reservoir, wherein the contact section is located between the first section and the second section.

10. The device according to claim 1, wherein the detector includes at least one of a magnetic, an optic, and a mechanical detector for detecting the changes in the form of the leaf spring member.

11. The device according to claim 1, further comprising a processing unit for receiving an electric signal from the detector and for transforming the electric signal into a fill level of the flexible medicine reservoir.

12. The device of claim 1 in which the leaf spring member is continuously in contact with the floating bearing for all conditions of the flexible medicine reservoir from an empty condition to a full condition.

13. The device according to claim 1, wherein the detector includes a magnetic sensor fixedly arranged with respect to the support, wherein the magnetic sensor is designed to cooperate with a magnetic element which is fixed to the leaf spring member in such a manner that the magnetic element follows a rotational motion of the first part effected because of the changes of the form of the leaf spring member.

14. The device according to claim 13, wherein the floating bearing is a slide bearing, the second section being connected to a guided section that can slide along a fixed portion that is fixedly arranged relative to the support.

15. A medical infusion device comprising a device according to claim 1 and a medical pump, wherein the flexible medicine reservoir is designed to deliver medicine to the medical pump and/or to receive medicine from the medical pump.

16. The medical infusion device according to claim 15, wherein the medical pump is an insulin pump, and wherein the flexible medicine reservoir is designed to store a medicine that includes insulin.

17. A device for measuring a fill level of a flexible medicine reservoir, comprising:
   a support for supporting the flexible medicine reservoir;
   a leaf spring member having a form,
      wherein a first section of the leaf spring member is mounted to a fixed bearing, wherein a second section of the leaf spring member is guided by a floating bearing, wherein the floating bearing is a slide bearing, the second section being connected to a guided section that can slide along a fixed portion that is fixedly arranged relative to the support,
      wherein the leaf spring member is designed for contacting the flexible medicine reservoir, changes in the fill level of the flexible medicine reservoir effecting changes of the form of the leaf spring member, and;
   a detector arranged for detecting the effected changes of the form of the leaf spring member and for enabling measuring of the fill level of the flexible medicine reservoir, wherein the detector is designed for detecting a rotational motion of the first section about the fixed bearing.

18. A device for measuring a fill level of a flexible medicine reservoir, comprising:
   a support for supporting the flexible medicine reservoir;
   a leaf spring member having a form,
      wherein a first section of the leaf spring member is mounted to a fixed bearing, wherein a second section of the leaf spring member is guided by a floating bearing, wherein the leaf spring member is designed for contacting the flexible medicine reservoir, changes in the fill level of the flexible medicine reservoir effecting changes of the form of the leaf spring member, and;

a detector arranged for detecting the effected changes of the form of the leaf spring member and for enabling measuring of the fill level of the flexible medicine reservoir, wherein the detector is designed for detecting a rotational motion of the first section about the fixed bearing.

19. The device according to claim 18, wherein the fixed bearing is a hinge bearing, the first section being connected to one or more barrel sections that are rotationally mounted on a pivot that is fixedly arranged with respect to the support.

20. The device according to claim 18, wherein the detector includes a magnetic sensor fixedly arranged with respect to the support, wherein the magnetic sensor is designed to cooperate with a magnetic element which is fixed to the leaf spring member in such a manner that the magnetic element follows a rotational motion of the first part effected because of the changes of the form of the leaf spring member.

21. The device according to claim 18, wherein the floating bearing is a slide bearing, the second section being connected to a guided section that can slide along a fixed portion that is fixedly arranged relative to the support.

* * * * *